United States Patent [19]

Tokumori et al.

[11] Patent Number: 4,562,071
[45] Date of Patent: Dec. 31, 1985

[54] METHOD OF TREATING DIABETIC NEPHROPATHY

[75] Inventors: Yutaka Tokumori, Yonago; Osamu Mokuda, Hyogo; Tadasu Ikeda, Yonago; Akira Takeda, Yonago; Masato Tominaga, Yonago; Hiroto Mashiba, Yonago, all of Japan

[73] Assignee: Eisai Co., Ltd., Tokyo, Japan

[21] Appl. No.: 498,237

[22] Filed: May 26, 1983

[30] Foreign Application Priority Data

May 28, 1982 [JP] Japan ................................. 57-89808

[51] Int. Cl.⁴ ............................................ A61K 37/48
[52] U.S. Cl. ..................................................... 424/94
[58] Field of Search .......................................... 424/94

[56] References Cited
PUBLICATIONS

*Diabetes Mellitus,* Seventh Edition, 1967, Eli Lilly and Company.
Davies, M. et al., *Chemical Abstracts,* 89: 3835z, "The Degradation of Human Glomerular Basement Membrane with Purified Lysosomal Proteinases. Evidence for the Pathogenic Role of the Polymorphonuclear Leukocyte in Glomerulonephritis", vol. 89 (1978).
Oikawa, Shinichi et al., *Chemical Abstracts,* 97: 192934e, "Inhibitory Effect of Pancreatic Elastase on Thickening of the Renal Glomerular Basement Membrane in the Spontaneously Diabetic Rat", vol. 97 (1982).
Shibata, Masao et al., *Chemical Abstracts,* 95: 59421c, "Inhibitory Effect of Elastase on the Glomerular Capillary Basement Membrane Thickening of the Experimental Congenital Diabetic Mice (N.S.Y. Mice)", vol. 95 (1981).
Hasegawa, Osamu, *Chemical Abstracts,* 94: 169968y, "Two New Methods for the Determination of Serum Elastase Activity and Their Clinical Significances", vol. 94 (1981).
Ramamurthy, N. S. et al., *Chemical Abstracts,* 99: 3739c, "Diabetes Increases Collagenase Activity in Extracts of Rat Gingiva and Skin", vol. 99 (1983).
Tamura, Shinji et al., *Chemical Abstracts,* 99: 173903u, "Studies on Elastase in Diabetic Rats", vol. 99 (1983).
Starkey, Phyllis M., *Chemical Abstracts,* 89: 125187k, "The Effect of Human Neutrophil Elastase and Cathepsin G on the Collagen of Cartilage, Tendon, and Cornea", vol. 89 (1978).
Davies, Malcom, et al., *Chemical Abstracts,* 94: 154025q, "The Binding of Human Lysosomal Elastase to Glomerular Basement Membrane", vol. 94 (1981).
Stuffers-Heiman, Marianne et al., *Chemical Abstracts,* 92: 108873a, "Immunological Properties of Glomerular Basement Membrane Antigens Solubilized by Elastase Digestion", vol. 92 (1980).
Matsutani et al.-Chem. Abst., vol. 98 (1983), p. 155,080y.
Oikawa et al.-Chem. Abst., vol. 92 (1980), p. 108570z.

*Primary Examiner*—Sam Rosen
*Attorney, Agent, or Firm*—Flynn, Thiel, Boutell & Tanis

[57] ABSTRACT

A therapeutic agent for the treatment of diabetic nephropathy is disclosed which contains elastase as active ingredient.

11 Claims, 2 Drawing Figures

METHOD OF TREATING DIABETIC NEPHROPATHY

This invention relates to a therapeutic agent for treating diabetic nephropathy and which contains elastase as active ingredient Marked progress has been made recently in the therapeutic technology for treatment of diabetes, such as the preparation of purified insulin, and the development of human insulin and artificial pancreas. However, it is impossible to perfectly prevent advancement of diabetic microangiopathy by a combination of the currently practiced therapeutic methods for treating diabetes, that is, diet therapy, oral administration of a blood sugar level lowering agent and subcutaneous injection of insulin.

In particular, diabetic nephropathy, which is a typical type of microangiopathy, is one of the principal causes of death of diabetics and is drawing keen attention as a factor which influences the prognosis of diabetic patients.

Disturbance of metabolism is considered to be the most likely cause of diabetic nephropathy, and therefore, basically, correction of metabolic abnormalities, in other words, perfect subdual of diabetes, is necessary for the prevention of diabetic nephropathy. At present, however, no effective method is available, except for certain specific measures, such as the use of an artificial pancreas, for complete correction of metabolic abnormalities due to diabetes, and, hence, there is no alternative other than to take prophylactic measures against nephropathy by accepting some degree of metabolic abnormalities as inevitable. Under these circumstances, there have been proposed and practiced various prophylactic measures, such as hypophysectomy, renal transplantation, use of a non-steroidal anti-inflammatory agent, or anticoagulative therapy, but a decisive therapy has not yet been established, and at present, there is no option except eventually to resort to artificial dialysis for patients whose condition has advanced to renal failure.

In view of these circumstances, the inventor has investigated with a view to discovering a pharmaceutical agent capable of alleviating or curing diabetic nephropathy, in particular, a therapeutic agent capable of decreasing proteinuria and serumuria nitrogen which are typical clinico-chemical indications of diabetic nephropathy and, as a result, it was found that elastase can attain this object. The present invention was completed on the basis of this discovery.

Thus, the object of this invention is to provide a pharmaceutical agent which is effective for controlling, alleviating or curing diabetic nephropathy, especially for decreasing proteinuria and serumuria nitrogen which is a clinico-chemical indication or feature of diabetic nephropathy.

Elastase is a known enzyme which specifically decomposes elastin, a hard protein insoluble in water. Elastase is industrially produced by extraction from swine pancreas. This enzyme is characterized by the following properties.

It has a molecular weight of 25,900 (as determined from the amino acid sequence of the primary structure) and the pH of its isoelectric point is $9.5\pm0.5$. Its sedimentation coefficient ($S_{20}$, w) is 2.6. As for its activity, it contains serine and histidine at its active center. In addition to elastin, it can specifically decompose N-$\alpha$-benzoyl-L-alanine methyl ester or acetyl-L-trialanine p-nitroanilide, as a synthetic substrate. According to the results of an assay using N-$\alpha$-benzoyl-L-alanine methyl ester as the substrate, the optimum pH for activity is 8 to 10, particularly around 8.8. It was also found that this enzyme is inhibited in its activity by NaCl, KCl, $(NH_4)_2SO_4$, NaCN and $CuSO_4$ as well as by some kinds of N-$\alpha$-benzoylcarboxy derivatives. Porcine elastase is preferably used in the present invention.

Biochemically, elastase is found to have a $\beta$-lipoproteinase activity and a lipoprotein lipase activity, and it also exhibits a normalizing action on disturbed lipid metabolism in the sera or tissues. Therefore, this enzyme can be clinically used for improving serolipid abnormality concomitant with hyperlipidemia or arteriosclerosis. It also acts on the artery wall itself so as to maintain or elevate the elasticity or extensibility of the artery wall. In other words, it removes degenerated elastin in the artery wall whereby to promote formation of fresh elastin, while also controlling deposition of fat on the degenerated elastin to prevent occurrence of atherosclerosis.

Some of the relevant literature on elastase is listed below:

(1) K. Ogawa and Y. Gogo, "A morphological study on the anti-atherosclerotic action of elastase", Nihon Ronen Igakkai Zasshi, Vol. 10, 277-292 (1973).

(2) A. Osawa, "On the anti-arteriosclerotic action of elastase", Nihon Naika Gakkai Zasshi, Vol. 59, 20-29 (1970).

(3) S. Naito, T. Azumano, T. Iwabuchi, Y. Ishimaru, M. Uesugi, M. Ogasawara, M. Omori, M. Kato, H. Kimura, S. Shichiri and S. Yokoyama, "A study on the serolipid abnormality improving effect of elastase by double blind test", Igaku no Ayumi, Vol. 82, 848-859 (1972).

Considering the various functions of elastase comprehensively, it becomes apparent that this enzyme not only is efficacious against hyperlipidemia, arteriosclerosis and hypertension, but also is effective for the treatment of diabetes.

For example, it has been reported recently that elastase showed a morphological lesion-controlling action in renal glomerules, such as thickening of a basal membrane, in a test on KK mice suffering from spontaneous diabetes. Another report disclosed that elastase not only had arrested increase of thickening of the basal membrane, but also showed a tendency even to lessen such thickening in tests on rats and N.S.Y. mice suffering from spontaneous diabetes.

The relevant literature on such research includes:

(4) S. Oikawa, M. Kakisaki and Y. Goto, "Control of thickening of basal membranes of renal glomerules of rats suffering from spontaneous diabetes by pancreatic elastase", Igaku no Ayumi, Vol. 111, 583-584 (1979).

(5) N. Kaseta, "Effect of elastase on early-phase renal lesion of KK mice suffering from spontaneous diabetes—A morphological observation by an electron microscope—", Rinsho Seijinbyo, Vol. 7, 133-139 (1977).

(6) M. Shibata, A. Kawanishi, T. Kishi, K. Kobayashi, B. Yasuda, T. Hisano and M. Sasaki, "Influence of elastase on glomerular lesion of N.S.Y. mice suffering from spontaneous diabetes", Nagoya J. Med. Sci., Vol. 43, 111 (1981).

The findings in the prior art, however, are related to diabetes in animals, such as rats and mice, and it is not yet known whether elastase is efficacious against human diabetes and concomitant renal problems.

Since Kimmelstiel and Wilson characterized modular sclerotic lesion in renal glomerules as a morphological change of the kidney in diabetic nephropathy in 1936, research has focused on the renal glomerular lesion and a great number of relevant reports have been published. It is believed that the earliest morphological change seen in the renal glomerules for human diabetes is thickening of the basal membrane of the wall of the glomerular loop.

However, it has not been determined whether or not elastase is effective to decrease urinary protein and serumuria nitrogen, which are typical clinico-chemical indications of human diabetic nephropathy.

Under these circumstances, the present invention has provided a new approach to the therapeutic treatment of diabetic nephropathy, and its prominent usefulness is clear from the fact that this invention makes it possible to therapeutically reduce urinary protein and serumuria nitrogen, the elimination of which in diabetic nephropathy have been hitherto considered to be very difficult.

Figure 2:
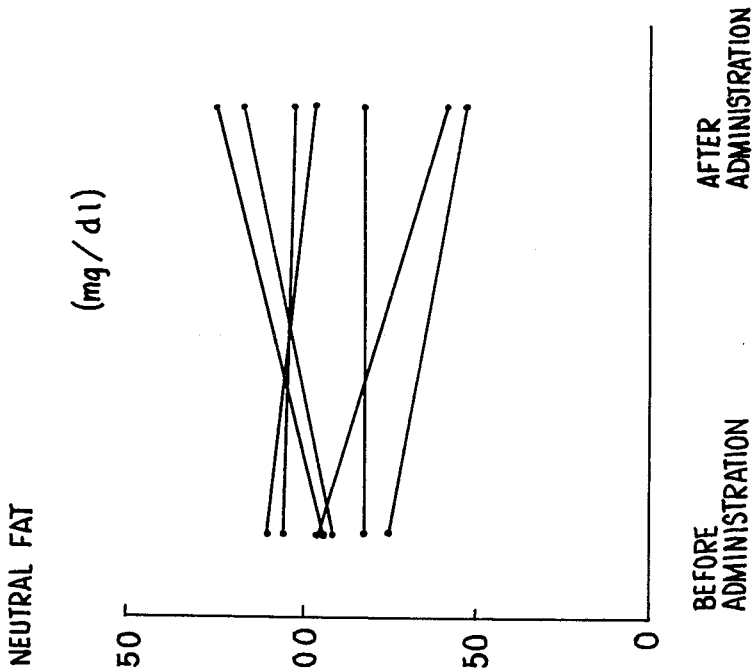
FIG. 2 shows the change in neutral fat for the patients tested in the Experimental Examples.

The "diabetic nephropathy" referred to in this description is a type of renal failure caused by diabetes. It defies precise definition, but diagnostically it includes cases which fall under any one of the following three categories. The application of this invention, however, is not limited to these cases:

(1) The patient has no past history of renal diseases, such as nephritis or nephrotic syndrome (primary), and no lesion is present which can cause prerenal proteinuria, such as heart failure, or postrenal proteinuria, such as crystitis, but the patient has persistent proteinuria.

(2) The patient shows no conspicuous abnormality such as cylinduria or hemoturia in the urinary sedimentation test.

(3) The patient had diabetic retinitis which preceded persistent proteinuria.

In the present invention, elastase is administered orally (per os). After being taken p.o., the elastase is absorbed into intestinal walls and is carried into the blood by passing through portal veins and lymphatic vessels. In the serum, it is combined with $\alpha_2$-macroglobulin and $\alpha_1$-antitrypsin and is distributed throughout the whole tissues. It is then metabolized chiefly in the liver and is excreted into the urine. Its concentration in the blood reaches a maximum six hours after administration, and the area below the in-blood concentration curve, which indicates the amount of elastase absorption by the blood, increases in proportion to the dosage.

In the present invention, the daily dosage of elastase is, for example, in the range of 5,000 to 20,000 EL.U. (elastase units) to a human patient suffering from diabetic nephropathy. It is preferably given daily for a period of, for example, 4 to 20 weeks at this dosage. The applications of this invention, however, are not limited to the above-defined ranges.

The acute toxicity of elastase is shown in the following table.

| Animal species | Sex | Acute toxicity $LD_{50}$ (EL.U./kg) | | | |
|---|---|---|---|---|---|
| | | Peroral | Subcutaneous | Intra-peritoneal | Intra-venous |
| Rat | M | >150,000 | >75,000 | 6,380 | 6,380 |
| | F | >150,000 | >75,000 | 5,850 | 6,380 |
| Mouse | M | >150,000 | >75,000 | 4,970 | 5,100 |
| | F | >150,000 | >75,000 | 2,780 | 4,310 |

Other types of toxicity were determined from further experiments described below.

Subacute toxicity

Elastase was administered, per os, to Wistar rats, both male and female, at doses of 750, 7,500, 37,500 and 75,000 EL.U./kg/day for 4 weeks continuously and to beagle dogs at doses of 900 and 4,500 EL.U./kg/day for 12 weeks continuously.

As a result, both the rats and beagle dogs showed no noteworthy abnormalities in their general physical state, blood and urine examinations and morphological observations (macroscopic and histological).

Chronic toxicity

Elastase was administered, per os, to Wistar rats, both male and female, at doses of 2,250, 5,700, 11,250 and 22,500 EL.U./kg/day for 24 weeks continuously. No noteworthy abnormalities were observed in the general physical state, blood and urine tests and morphological observations (macroscopic and histological) of the rats.

Teratogenicity

Elastase was administered, per os, to pregnant mice and rats during the organogenetic period at doses of 750, 7,500 and 75,000 EL.U./kg/day for 6 days continuously. As a result, no fetus death, no growth inhibitory and teratogenic action, and no influence on the morphological and functional differentiation of the newborn were observed.

Since the therapeutic agent of this invention is administered per os, it is preferably formed into a solid preparation suited for this purpose, such as granules, tablets or capsules. For making these solid preparations, there can be employed techniques commonly used in the art of drug formulation using an ordinary excipient. For example, granules can be formed by adding a binder directly or by fluidized bed spraying to a mixture of elastase, lactose, starch and cellulose and, if desired, these granules can be encapsulated.

The effect of this invention will now be further described by reference to experimental examples.

Experimental Examples

Subject and Method 13 patients having diabetic nephropathy (8 men and 5 women) were selected as subjects. The clinical characteristics of the subjects are shown in Table 1.

TABLE 1

| Subject No. | Age | Sex | Years for which the subject suffered from diabetes in the past | Deviation from ideal body weight (%) | Blood pressure (mmHg) | Retinopathy (Scott) | Previous treatment |
|---|---|---|---|---|---|---|---|
| 1 | 72 | M | 20 | +15.9 | 158/90 | II | Insulin |
| 2 | 66 | F | 13 | +1.1 | 170/90 | II | Insulin |
| 3 | 64 | M | 11 | +1.0 | 180/80 | IV | Insulin |
| 4 | 69 | M | 12 | +1.6 | 140/70 | IIIa | Insulin |
| 5 | 68 | M | 8 | +8.1 | 158/86 | II | Insulin |
| 6 | 58 | F | 11 | +12.3 | 150/80 | IV | Insulin |
| 7 | 72 | M | 9 | −8.0 | 140/70 | II | Oral hypoglycemic agents |
| 8 | 63 | M | 13 | +2.7 | 170/80 | IIIa | Oral hypoglycemic agents |
| 9 | 54 | M | 15 | +6.1 | 154/90 | IV | Oral hypoglycemic agents |
| 10 | 59 | F | 9 | −2.0 | 130/80 | IIIa | Insulin |
| 11 | 61 | F | 15 | +35.9 | 180/100 | IV | Insulin |
| 12 | 63 | F | 20 | −5.4 | 190/80 | Va | Insulin |
| 13 | 42 | M | 14 | +11.0 | 170/96 | IIIb | Insulin |

The subjects were diagnosed as having diabetic nephropathy only when all of the following three conditions were met:

(1) The subject had no past history of renal diseases, such as nephritis or nephrotic syndrome (primary), had no lesion causative of prerenal proteinuria, such as heart failure, or postrenal proteinuria, such as cystitis, but had persistent proteinuria.

(2) The subject showed no conspicuous abnormality such as cylinduria or hemoturia in the urinary sedimentation test.

(3) The subject had diabetic retinitis which preceded persistent proteinuria.

Elastase was administered to the above subjects at a rate of 10,800 EL.U. per day for a period of 12 weeks. The daily excretion of urinary protein and serumuria nitrogen before and after the administration were measured. In addition, fasting blood sugar, serum creatine and serum lipid (total cholesterol and neutral fats) were also measured for reference.

Results

Figure 1:
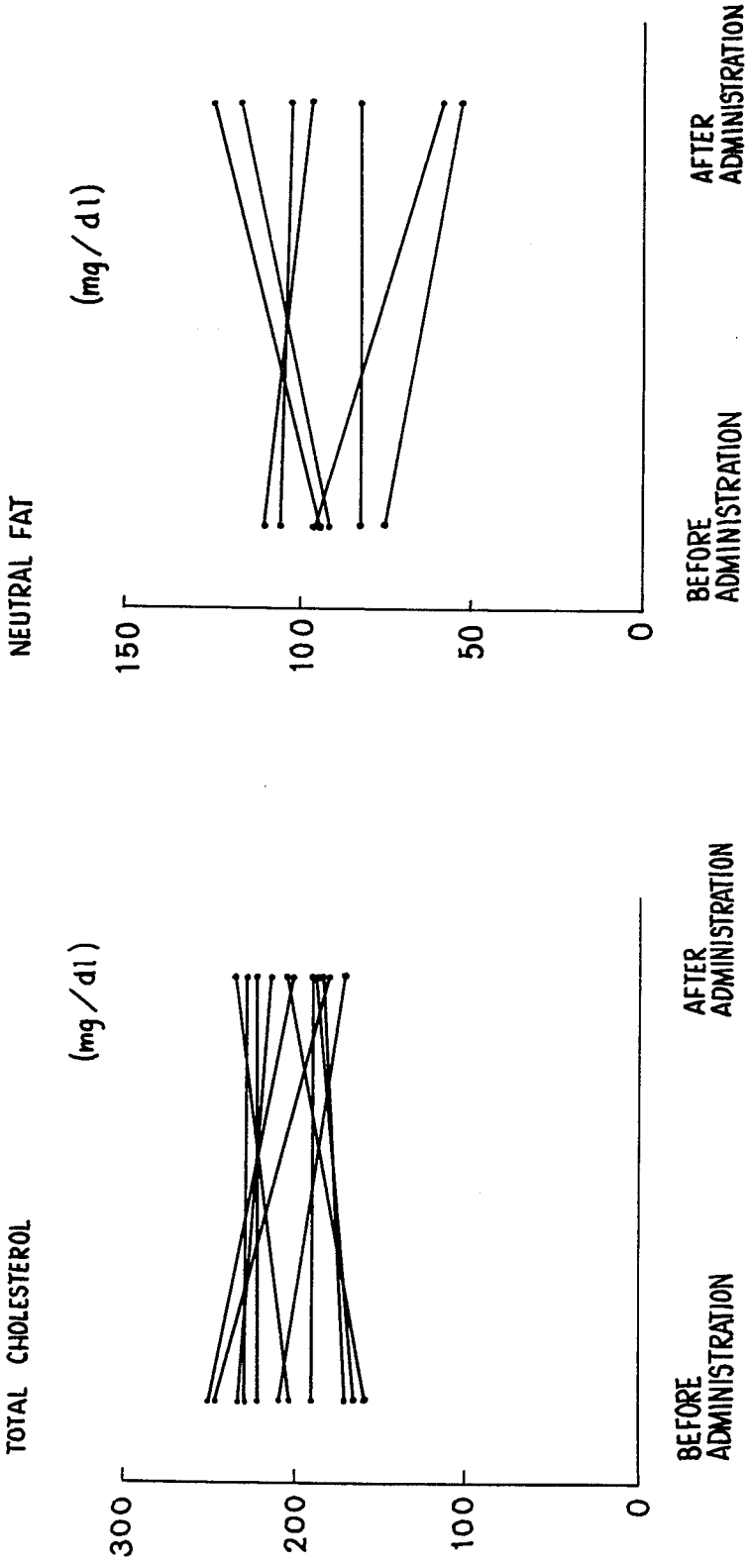
FIG. 1 shows the change in total cholesterol for the patients tested in the Experimental Examples.

The results are shown in Table 2 and FIG. 1.

(1) Changes in urinary protein excretion

As will be noted by comparing the daily amounts of urinary protein excretion before and after administration of elastase shown in Table 2, a significant decrease in the protein excretion occurred after administration of elastase in 5 out of the 13 subjects tested, and a tendency towards decreased urinary protein excretion was seen in 6 out of the remaining 8 subjects.

(2) Serumuria nitrogen

As seen in Table 2, 10 out of the 13 subjects showed decreases in serumuria nitrogen level, and these decreases were also observed for 3 out of the 5 subjects who showed a significant decrease in urinary protein excretion after administration of elastase.

(3) Other findings

As seen in Table 2, the serum creatine level remained substantially unchanged on the whole, although some subjects showed a slight drop of serum creatine level. Regarding changes in fasting blood sugar level (mean value of 3 to 4 measurements) before and after administration of elastase, no significant change was observed for all the cases. Also, as shown by FIG. 1 and FIG. 2, no subject had an abnormally high level of total cholesterol or neutral fat in the serum before administration of elastase, and no significant increase or decrease in these levels was observed after administration of elastase.

TABLE 2

| Case No. | Urinary protein excretion (g/day) | | Serumuria nitrogen level (mg/dl) | | Serum creatine level (mg/dl) | | Fasting blood sugar level (mg/dl) | |
|---|---|---|---|---|---|---|---|---|
| | Before administration | After administration | Before administration | After administration | Before administration | After administration | Before administration | After administration |
| 1 | 0.98 ± 0.21 | 0.55 ± 0.10* | 40 | 31 | 2.2 | 2.0 | 121 ± 4 | 117 ± 24 |
| 2 | 4.94 ± 2.50 | 2.87 ± 0.80 | 26 | 17 | 0.8 | 0.6 | 125 ± 30 | 101 ± 19 |
| 3 | 7.32 ± 1.90 | 3.76 ± 0.30 | 43 | 32 | 2.1 | 2.0 | 104 ± 9 | 105 ± 27 |
| 4 | 9.23 ± 0.44 | 5.42 ± 1.28** | 21 | 23 | 1.1 | 1.1 | 153 ± 31 | 148 ± 16 |
| 5 | 0.71 ± 0.50 | 1.78 ± 0.60** | 16 | 18 | 0.8 | 0.8 | 201 ± 41 | 172 ± 63 |
| 6 | 0.41 ± 0.12 | 0.21 ± 0.05 | 21 | 14 | 1.2 | 0.7 | 172 ± 24 | 141 ± 34 |
| 7 | 0.12 ± 0.04 | 0.14 ± 0.07 | 27 | 19 | 1.1 | 0.9 | 106 ± 19 | 125 ± 14 |
| 8 | 3.01 ± 0.08 | 0.78 ± 0.26* | 24 | 21 | 0.9 | 0.8 | 129 ± 11 | 122 ± 11 |
| 9 | 2.16 ± 0.64 | 1.90 ± 0.09 | 18 | 12 | 0.7 | 0.7 | 175 ± 12 | 180 ± 26 |
| 10 | 0.44 ± 0.07 | 0.27 ± 0.05* | 25 | 27 | 1.0 | 0.8 | 243 ± 14 | 216 ± 27 |
| 11 | 6.51 ± 1.19 | 3.29 ± 0.85* | 27 | 23 | 1.0 | 1.4 | 187 ± 30 | 184 ± 25 |
| 12 | 3.07 ± 0.40 | 2.57 ± 0.55 | 29 | 22 | 1.3 | 1.5 | 134 ± 87 | 159 ± 47 |
| 13 | 7.10 ± 0.85 | 6.30 ± 2.44 | 32 | 29 | 2.7 | 2.6 | 130 ± 35 | 110 ± 3 |

(Mean ± SD)

*$P < 0.02$
**$P < 0.01$

None of the subjects showed side effects which could be attributed to the therapeutic agent of this invention.

The present invention will be described in further detail hereinbelow by reference to illustrative examples.

Example 1

100 g of elastase (85 EL.U./mg) and 400 g of sucrose fatty acid ester were lightly triturated to form a uniform powder, and with this powder were mixed 500 g of spray-dried lactose, 495 g of crystalline cellulose and 400 g of calcium CMC (carboxymethyl cellulose). Then, 5 g of calcium stearate was sprinkled through an 80-mesh screen and mixed uniformly with the foregoing ingredients, and the mixture was worked into tablets each having a diameter of 8 mm and a weight of 180 mg for use as a treating agent for diabetic nephropathy.

Example 2

| Non-paril | 2.5 kg |
|---|---|
| HPC-L | 0.5 kg |
| ethanol | suitable quantity |
| elastase (85 EL.U./mg) | 0.6 kg |
| sucrose fatty acid ester | 1.5 kg |
| corn starch | 2.7 kg |
| HP-55 | 1.95 kg |
| acetyl monoglyceride | 0.25 kg |

Non-paril was charged in a centrifugal flow coating apparatus. While an ethanol solution of HPC-L was sprayed thereon, a mixed powder of elastase, sucrose fatty acid ester and corn starch was applied thereto and the mixture was granulated. The formed granules were spray-coated with an ethanol solution of acetyl monoglyceride and HP-55 using the same apparatus to produce enteric granules.

Non-paril is a mixture of sucrose and corn starch, HPC-L is hydroxypropylcellulose, and HP-55 is hydroxypropylmethylcellulose phthalate.

What is claimed is:

1. A method for treatment of diabetic nephropathy characterized by persistent proteinuria and serumuria nitrogen in a human patient, comprising administering to a human patient who is exhibiting persistent proteinuria and serumuria nitrogen that are clinically indicative of diabetic nephropathy, a composition containing elastase as an active ingredient in an amount effective to reduce the level of urinary protein excretion and serumuria nitrogen, in combination with a pharmacologically acceptable carrier, diluent, or vehicle.

2. A method as claimed in claim 1, wherein said patient suffering from diabetic nephropathy has persistent proteinuria, and: (1) said patient has no previous renal disease or lesions capable of causing prerenal proteinuria or postrenal proteinuria; (2) said patient has no conspicuous abnormalities detectable by a urinary sedimentation test; or (3) said patient suffered from diabetic retinitus which preceded said persistent proteinuria.

3. A method as claimed in claim 1, wherein said composition is administered orally.

4. A method as claimed in claim 3, wherein said composition is in the form of a powder, tablet or capsule.

5. A method as claimed in claim 1, wherein said composition is administered in an amount such that said patient receives a daily dosage of 5,000 to 20,000 elastase units.

6. A method as claimed in claim 5, wherein said daily dosage is administered over a period in the range of 4 to 20 weeks.

7. A method as claimed in claim 1, wherein said elastase has a molecular weight of 25,900, an isoelectric point pH of approximately 9.5, and a sedimentation coefficient $(S_{20}, w)$ of 2.6.

8. A method as claimed in claim 1, wherein said elastase is porcine elastase.

9. A method for the reduction of levels of urinary protein excretion and serumuria nitrogen in a human patient suffering from diabetic nephropathy, comprising administering to said patient an effective amount of a composition consisting essentially of elastase as an effective ingredient, in combination with a pharmacologically acceptable carrier, diluent, or vehicle, by oral administration.

10. A method of treating diabetic nephropathy, which comprises orally administering daily to a human being afflicted with diabetic nephropathy, over a period of at least several weeks, a therapeutically effective amount, for chronic treatment to reduce the levels of urinary protein excretion and serumuria nitrogen, of elastase in combination with a pharmacologically acceptable carrier, diluent or vehicle.

11. A method as claimed in claim 10 in which said therapeutically effective amount of elastase is in the range of from 5,000 to 20,000 elastase units per day.

* * * * *